(12) United States Patent
Majima

(10) Patent No.: US 6,314,944 B1
(45) Date of Patent: Nov. 13, 2001

(54) FUEL PROPERTY DETERMINATION FROM ACCUMULATED INTAKE AIR AMOUNT AND ACCUMULATED FUEL SUPPLY AMOUNT

(75) Inventor: Yoshihiro Majima, Inuyama (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/619,495

(22) Filed: Jul. 19, 2000

(30) Foreign Application Priority Data

Jul. 30, 1999 (JP) .................................................. 11-216173
May 24, 2000 (JP) .................................................. 12-157940

(51) Int. Cl.[7] .......................... F02M 51/00; G01N 33/22
(52) U.S. Cl. ......................... 123/491; 123/1 A; 73/35.02; 73/117.3
(58) Field of Search .................... 123/49, 1 A; 73/35.02, 73/117.3

(56) References Cited

U.S. PATENT DOCUMENTS

| 5,111,796 | * | 5/1992 | Ogita | 123/520 |
| 5,345,908 | | 9/1994 | Nishimura et al. | |
| 5,711,272 | * | 1/1998 | Maegawa et al. | 123/1 A |
| 6,109,225 | * | 8/2000 | Ogita et al. | 123/90.15 |

FOREIGN PATENT DOCUMENTS 5-65838  3/1993 (JP) .

* cited by examiner

*Primary Examiner*—Erick Solis
(74) *Attorney, Agent, or Firm*—Nixon & Vanderhye P.C.

(57) ABSTRACT

In a fuel supply control for engines, the amount of fuel supplied to the engine is corrected based on property of fuel which is determined immediately after engine starting. The fuel property is determined based on the amount of fuel injected, but remaining upstream the cylinder and not burned in a cylinder. This fuel property value TNEN is estimated from an accumulated intake air amount TAF and an accumulated fuel injection amount TTAU as TNEN= TTAU·14.7−TTAF. In the above equation, 14.7 indicates the stoichiometric air-fuel ratio to which the air-fuel ratio of air-fuel mixture is controlled while the accumulated intake air amount and the accumulated fuel injection amount are measured. If the calculated value indicates that the fuel is a heavy type, the amount of fuel injected in the next engine starting operation is increased to compensate for the amount of fuel which will remain upstream the cylinder. Alternatively, the fuel property may be determined based on an increase of pressure in a fuel tank detected while the fuel tank is in a fully closed condition.

18 Claims, 12 Drawing Sheets

FIG. 7A

| TW (°C) | -40 | -20 | 0 | 20 | 40 | 60 |
|---|---|---|---|---|---|---|
| KTW | 0.85 | 0.9 | 0.95 | 1 | 1.05 | 1.1 |

FIG. 7B

| TAF (g) | 150 | 200 | 300 | 350 | 400 | 450 |
|---|---|---|---|---|---|---|
| KTAF | 0.95 | 1 | 1.05 | 1.1 | 1.15 | 1.2 |

FIG. 8

| TW (°C) | -20 | 0 | 20 | 40 | 60 |
|---|---|---|---|---|---|
| J | 3 | 2 | 1.0 | 0.5 | 0 |

FIG. 9

| PST (sec) | 0 | 10 | 20 |
|---|---|---|---|
| KTIM | 0.9 | 0.5 | 0.1 |

FIG. 12

| AF (g/s) \ NE (rpm) | 1000 | 2000 | 3000 | 4000 |
|---|---|---|---|---|
| 10 | 0.01 | 0.05 | ... | ... |
| 20 | 0.05 | 0.1 | ... | ... |
| 30 | ... | ... | ... | ... |
| 40 | ... | ... | ... | ... |
| 50 | ... | ... | ... | ... |

FUEL PROPERTY DETERMINATION FROM ACCUMULATED INTAKE AIR AMOUNT AND ACCUMULATED FUEL SUPPLY AMOUNT

CROSS REFERENCE TO RELATED APPLICATION

The present application relates to and incorporates herein by reference Japanese Patent Applications No. 11-216173 filed on Jul. 30, 1999 and No. 2000-157940 filed on May 24, 2000.

BACKGROUND OF THE INVENTION

The present invention relates to a fuel property determination method and apparatus for determining property of fuel supplied to internal combustion engines.

In gasoline engines mounted on vehicles, gasoline fuel is injected in intake ports of the engine by fuel injectors mounted on an intake pipe of the engine. Most of the injected fuel is directly sucked into cylinders of the engine. However, a part of the injected fuel remains on the inner peripheral walls of the intake port or on the surface of intake valves for a moment, and then gradually evaporates and enters the cylinders. Thus, the amount of fuel sucked into each cylinder varies with the amount of evaporation of fuel remaining on the inner peripheral wall or the like as the fuel wet.

The amount of evaporation, that is, speed of evaporation, depends on fuel property. The fuel property varies even among the same type of fuel and among fuel producers. It is also varied in dependence on season and sales area, even if the fuel is of the same producer's. It is therefore necessary to accurately determine the fuel property so that the air-fuel ratio of air-fuel mixture supplied to the engine may be accurately controlled in consideration of the amount of evaporation of fuel.

It is proposed to detect the fuel property by a fuel property sensor provided in a fuel tank. The fuel property sensor, however, adds cost.

It is also proposed in JP-A-5-65838 to measure a period required to complete engine cranking by increasing the amount of fuel at the time of engine starting, and to determine the fuel property based on the measured engine starting period. However, the engine starting period varies with engine coolant temperature and other factors other than the fuel property, thus disabling accurate determination of the fuel property from the measured engine starting period.

SUMMARY OF THE INVENTION

It is therefore an object of the present invention to provide a fuel property determination method and apparatus which is capable of accurately determining property of fuel supplied to engines.

According to a first aspect of the present invention, the amount of fuel supplied to the engine immediately after starting the engine is corrected based on property of fuel which is determined immediately after engine starting. The fuel property is determined based on the amount of fuel injected, but remaining upstream the cylinder and not burned in a cylinder. The fuel property is determined from an accumulated intake air amount and an accumulated fuel injection amount. If the calculated value indicates that the fuel is a heavy type, the amount of fuel injected in the next engine starting operation is increased to compensate for the amount of fuel which will remain upstream the cylinder.

According to a second aspect of the present invention, the fuel property is determined based on an increase of pressure in a fuel tank detected while the fuel tank is in a fully closed condition. Preferably, the detected increase in the pressure is corrected with a decrease of pressure in the fuel tank which results from supply of fuel from the fuel tank to the engine.

BRIEF DESCRIPTION OF THE DRAWINGS

The above and other objects, features and advantages of the present invention will become more apparent from the following detailed description made with reference to the accompanying drawings. In the drawings:

FIGS. 7A and 7B are mapped data tables showing relationship between a coolant temperature TW and a correction coefficient KTW used in the fuel property determination processing shown in FIG. 3 and between an accumulated intake air amount TAF and a correction coefficient KTAF used in the fuel property determination processing shown in FIG. 4, respectively;

FIG. 8 is a mapped data table showing a relationship between a coolant temperature TW and a comparison reference J used in the fuel property determination processing shown in FIG. 4;

FIG. 9 is a mapped data table showing a relation between a post-start time PST and a correction coefficient KTIM used in the correction amount calculation processing shown in FIG. 5;

FIG. 12 is a mapped data table showing a relation of a correction amount relative to an engine rotation speed NE and an intake air amount AF;

DETAILED DESCRIPTION OF THE PREFERRED EMBODIMENT

Figure 1:
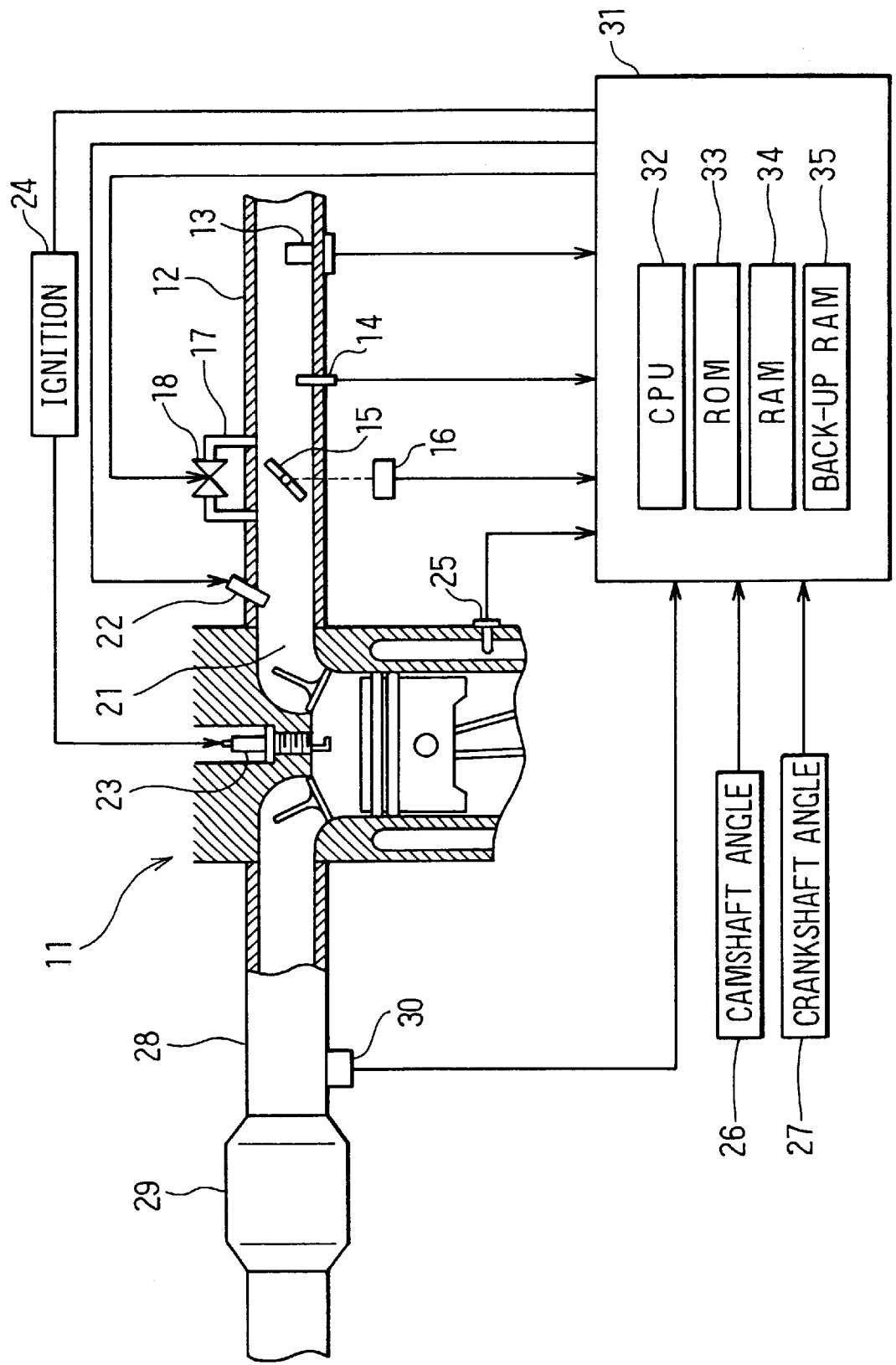
FIG. 1 is a schematic view showing an engine control system which employs a fuel property determination method and apparatus according to a first embodiment of the present invention.

The present invention is described in further detail with reference to various embodiments, in which the same or like reference numerals designate the same or like parts.

First Embodiment

Referring first to FIG. 1 showing a first embodiment, a gasoline engine 11 has an air cleaner (not shown) at the most upstream side of its intake pipe 12. An air flow sensor 13 is provided at the downstream of the air cleaner to detect the amount of intake air (AF) flowing in the intake pipe 12. An intake air temperature sensor 14 is provided at the downstream of the air flow sensor 13 to detect the temperature of the intake air. A throttle valve 15 and a throttle position sensor 16 are provided at the downstream of the temperature sensor 14. The throttle position sensor 16 is for detecting the opening position of the throttle valve 15.

A bypass air passage 17 is provided on the intake pipe 12 in such a manner to bypass the throttle valve 15. The bypass air passage 17 has an idle speed control (ISC) valve 18 which regulates the amount of bypass air flowing therethrough thereby to control an idle rotation speed of the engine 11.

A fuel injector 22 is mounted on an intake port 21 of each cylinder of the engine 11 to inject gasoline fuel in the intake port 21. A spark plug 23 is mounted in a cylinder head of each cylinder. The spark plug 23 is connected to an ignition device 24 which generates a high spark voltage to ignite air-fuel mixture supplied into the cylinder.

A coolant temperature sensor 25 is mounted on a cylinder block of the engine 11 to detect the temperature of coolant. The engine 11 is also provided with a camshaft angle sensor 26 and a crankshaft angle sensor 27. The camshaft angle sensor 26 is for generating a position signal as a cylinder discrimination signal at a predetermined camshaft rotation angle in each rotation of the camshaft. The crankshaft angle sensor 27 is for generating a series of position signals every predetermined angular rotation in each rotation of the crankshaft so that the rotation speed of the engine 11 may be detected based on the position signals.

A catalytic converter 29 accommodating a catalyst therein is provided in an exhaust pipe 28 of the engine 11. The catalytic converter 29 may be a three-way type which purifies exhaust emissions (CO, HC, NOx). An air-fuel ratio sensor 30 is mounted on the exhaust pipe 28 at the upstream of the catalytic converter 29 to detect the air-fuel ratio (A/F) of the air-fuel mixture based on the concentration of oxygen in the exhaust.

Those sensors are connected to an electronic engine control unit (ECU) 31, which includes a CPU 32, ROM 33 for storing control programs and data, RAM 34 for storing input data, calculation data and the like, and back-up RAM 35 for storing various data to be maintained even after an ignition switch (not shown) is turned off. The ECU 31, particularly CPU 32, calculates various control amounts based on the sensor output signals and controls fuel injection amount, ignition timing and idle rotation speed by the fuel injectors 22, ignition device 24 and ISC control valve 18.

Figure 2:
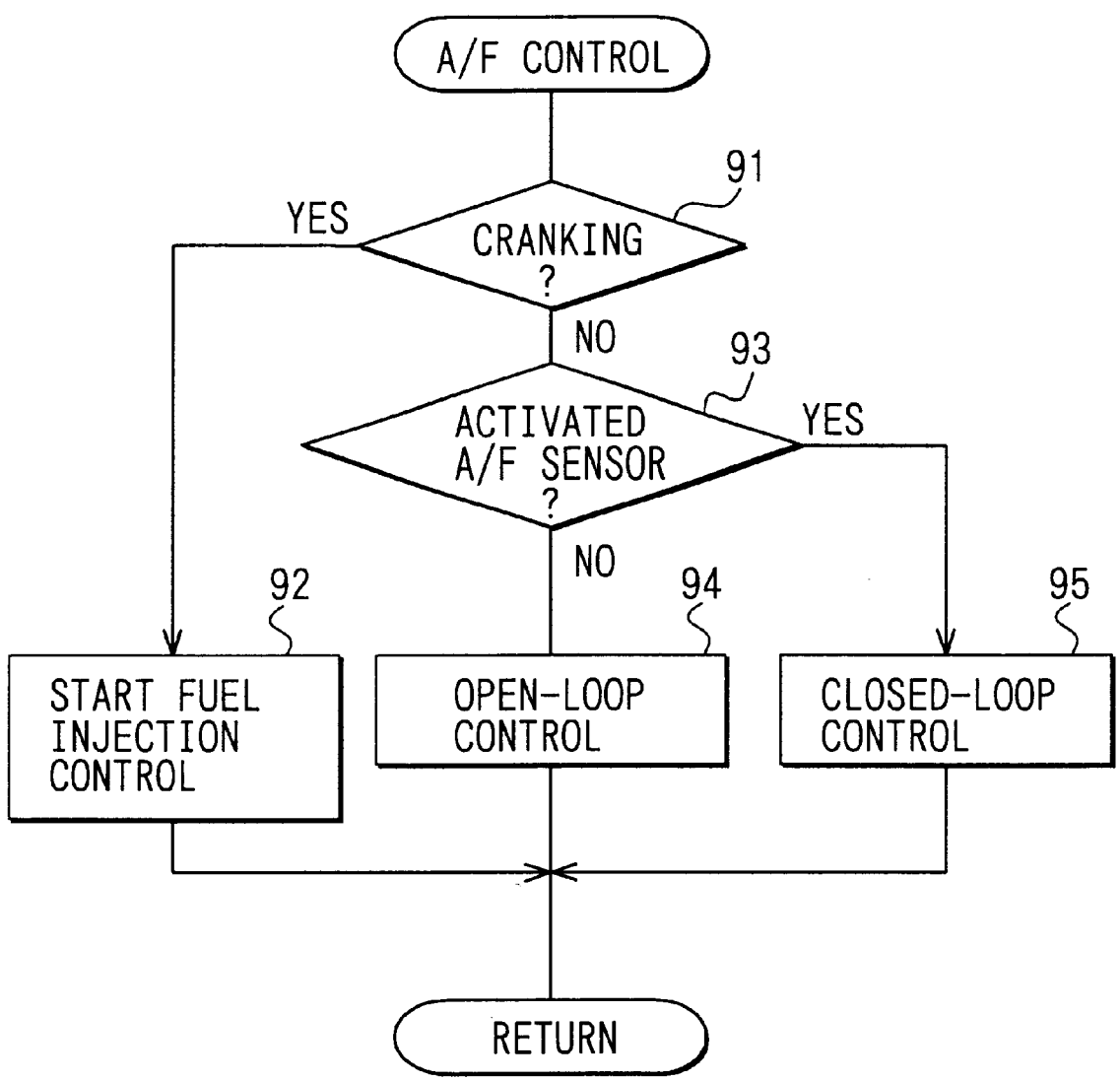
FIG. 2 is a flow diagram showing an air-fuel ratio control processing executed in the first embodiment.

The ECU 31 executes an air-fuel ratio control program shown in FIG. 2. The air-fuel ratio (A/F) is controlled by increasing or decreasing the amount of injected fuel. Specifically, the ECU 31 controls the air-fuel ratio of the air-fuel mixture to a predetermined air-fuel ratio in the open-loop manner after the engine 11 is started until the air-fuel ratio sensor 30 is activated. It controls the air-fuel ratio to the target air-fuel ratio in the closed-loop or feedback (F/B) manner after the air-fuel ratio sensor 30 is activated.

The air-fuel ratio control processing of FIG. 2 is executed by the CPU 32 every fixed angular rotation of the crankshaft or every fixed time period after the ignition switch is turned on. It is checked first at step 91 whether the engine 11 is in the cranking or starting condition, that is, whether starting the engine 11 has been completed. The cranking condition may be determined based on whether the engine rotation speed NE is below a predetermined comparison reference (for instance, 400 rpm). If the check result is YES (before completion of the engine starting), a start time fuel injection control is executed at step 92. It is assumed here that the fuel injection amount (time) at the time of starting the engine 11 is determined to attain the stoichiometric air-fuel ratio (14.7) at step 92.

If the check result at step 91 is NO (after completion of the engine starting), it is further checked at step 93 whether the air-fuel ratio sensor 30 has been activated. This checking may be made based on the impedance of a sensing element of the sensor 30. If the impedance is low indicating a sufficiently high temperature of the sensor 30, and the sensor 30 may be determined to have been activated.

If the check result at step 93 is NO (before activation), the air-fuel ratio control is executed at step 94 in the open-loop manner because the air-fuel ratio sensor 30 is still inoperative to detect the air-fuel ratio. In this open-loop control, it is also assumed that the fuel injection amount is calculated to attain the stoichiometric fuel ratio (14.7). Specifically, the fuel injection amount TAU is calculated as follows.

TAU=Tp+COEF+KTAU

In this equation, Tp indicates a basic fuel injection amount calculated from the intake air amount AF and the rotation speed NE, COEF indicates a fuel correction amount calculated from engine operating conditions such as the coolant temperature TW, and KTAU indicates another fuel correction amount calculated from the fuel property. The fuel correction amount KTAU is calculated in the fuel correction amount calculation processing shown in FIG. 5. The fuel correction amount is set to KTAU=0 if the fuel property is determined to be "light" in the fuel property determination processing shown in FIGS. 4 and 5.

If the check result at step 93 is YES (after activation), the air-fuel ratio is controlled to a target air-fuel ratio, stoichiometric ratio (14.7), in the closed-loop manner at step 95. That is, the fuel injection amount is increased and decreased as the detected air-fuel ratio is leaner and richer than the target ratio, respectively.

Figure 3:
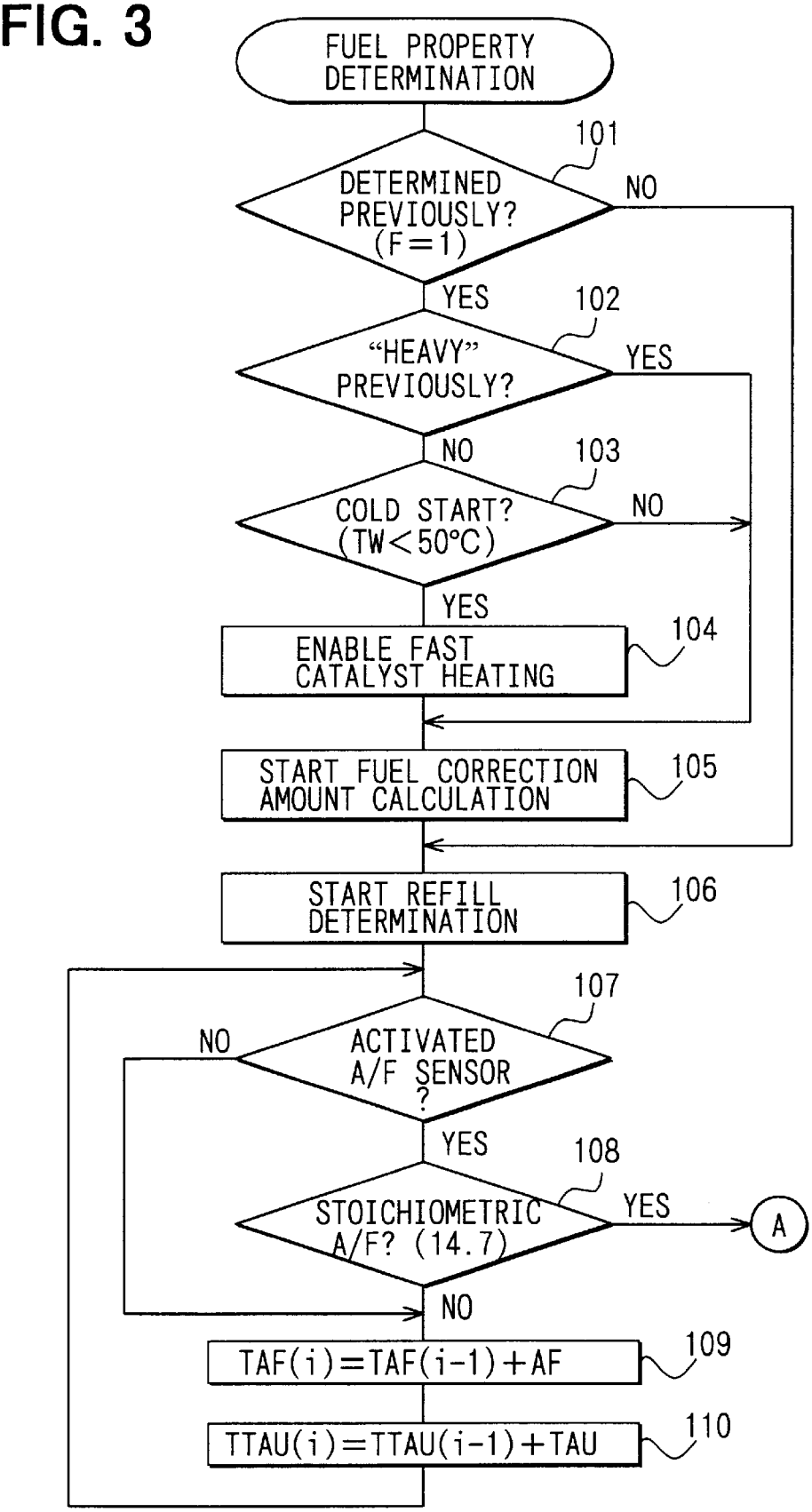
FIG. 3 is a flow diagram showing a part of a fuel property determination processing executed in the first embodiment.
Figure 4:
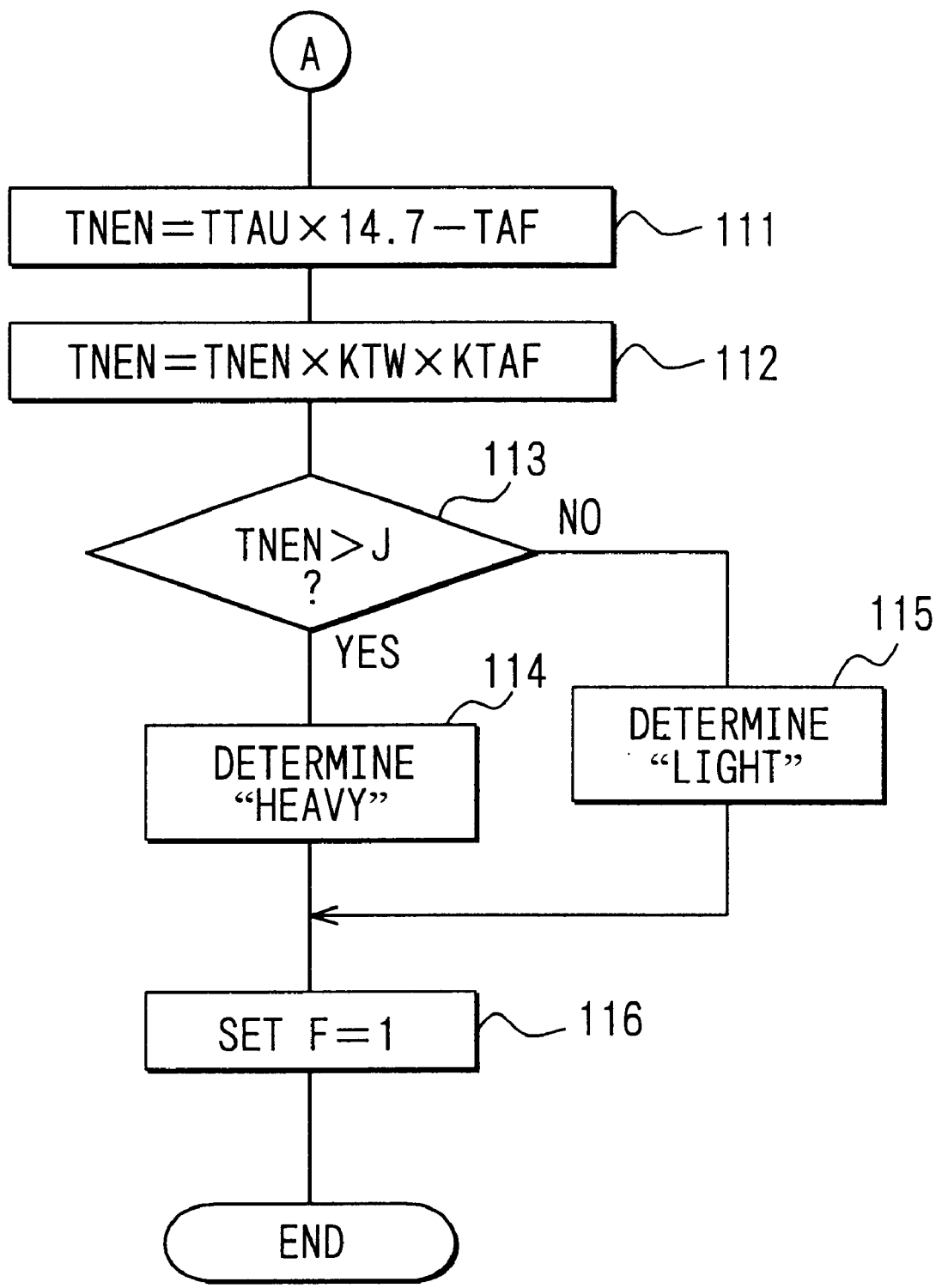
FIG. 4 is a flow diagram showing another part of the fuel property determination processing executed in the first embodiment.

The ECU 31 determines the fuel property as shown in FIGS. 3 and 4. In this processing, the detected amount of the intake air (AF) and the calculated amount of fuel injection (TAU) are accumulated, respectively, during a period from the detection of activation of the air-fuel ratio sensor 4 to the detection of the air-fuel ratio reaching the target air-fuel ratio. A fuel property value TNEN is calculated from the total or accumulated intake air amount TAF and the total or accumulated fuel injection amount TTAU. The fuel property, that is, light fuel or heavy fuel, is determined from the calculated fuel property value TNEN.

More specifically, the fuel property determination processing is initiated when the ignition switch is turned on. It is first checked at step 101 whether the fuel property has been determined in the previous engine starting time. This checking may be made with reference to a fuel property determination flag F stored in the back-up RAM 35 even when the engine 11 is not operated. The determination flag is set (F=1) when the fuel property has already been determined. If the check result is YES (F=1), it is further checked at step 102 whether the previous determination resulted in heavy fuel.

If the check result at step 102 is NO (light fuel), it is checked at step 103 whether the engine 11 is in the cold start operation. This checking may be made by comparing the detected coolant temperature TW with a comparison reference, for instance, 50° C. If the check result is YES (cold start), fast catalyst heating is enabled at step 104. The catalyst is heated to a higher temperature quickly by retarding the ignition timing than normal thereby to raise the temperature of exhaust gas.

If the check result at step 102 is YES (heavy fuel), the fast catalyst heating (step 104) is not effected. The heavy fuel is less evaporative. Therefore, the retarded ignition timing tends to cause incomplete combustion of the air-fuel mixture in the cylinder and lessen the engine starting operation. It is however possible to effect the fast catalyst heating by only slightly retarding the ignition timing not to lessen the combustion operation in the cylinder. Alternatively, the fast catalyst heating may be effected with the retarded ignition timing after a predetermined time, while disabling the ignition timing retardation until a certain amount of fuel accumulates on the inner wall of the intake port 21 after an initiation of the engine starting.

Further, if the check result at step 103 is NO (after cold starting), the fast catalyst heating (step 104) is not effected. If the engine 11 is not in the cold starting operation, it is assumed that the catalyst has already been heated sufficiently.

Figure 5:
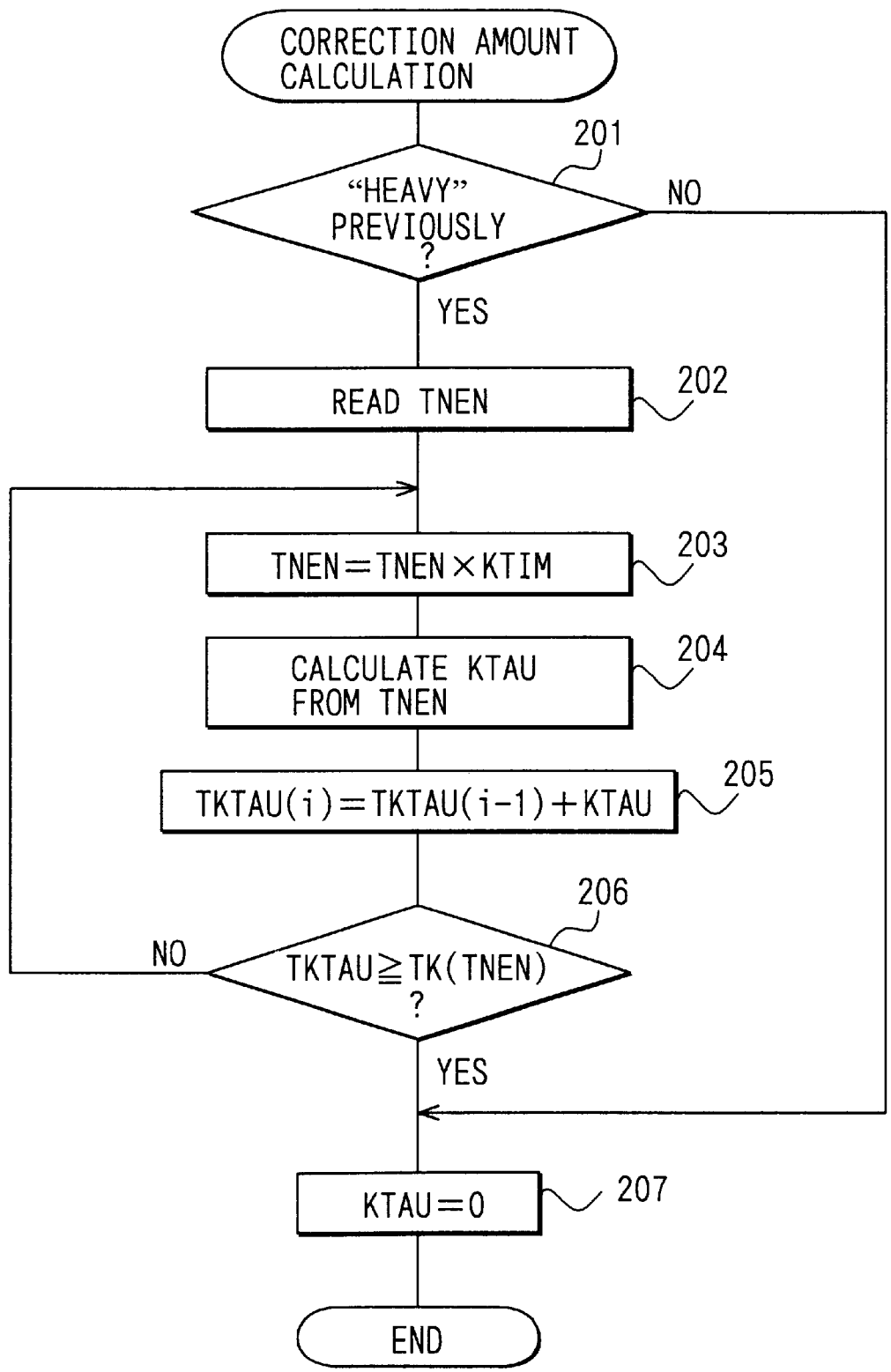
FIG. 5 is a flow diagram showing a correction amount calculation processing executed in the first embodiment.
Figure 6:
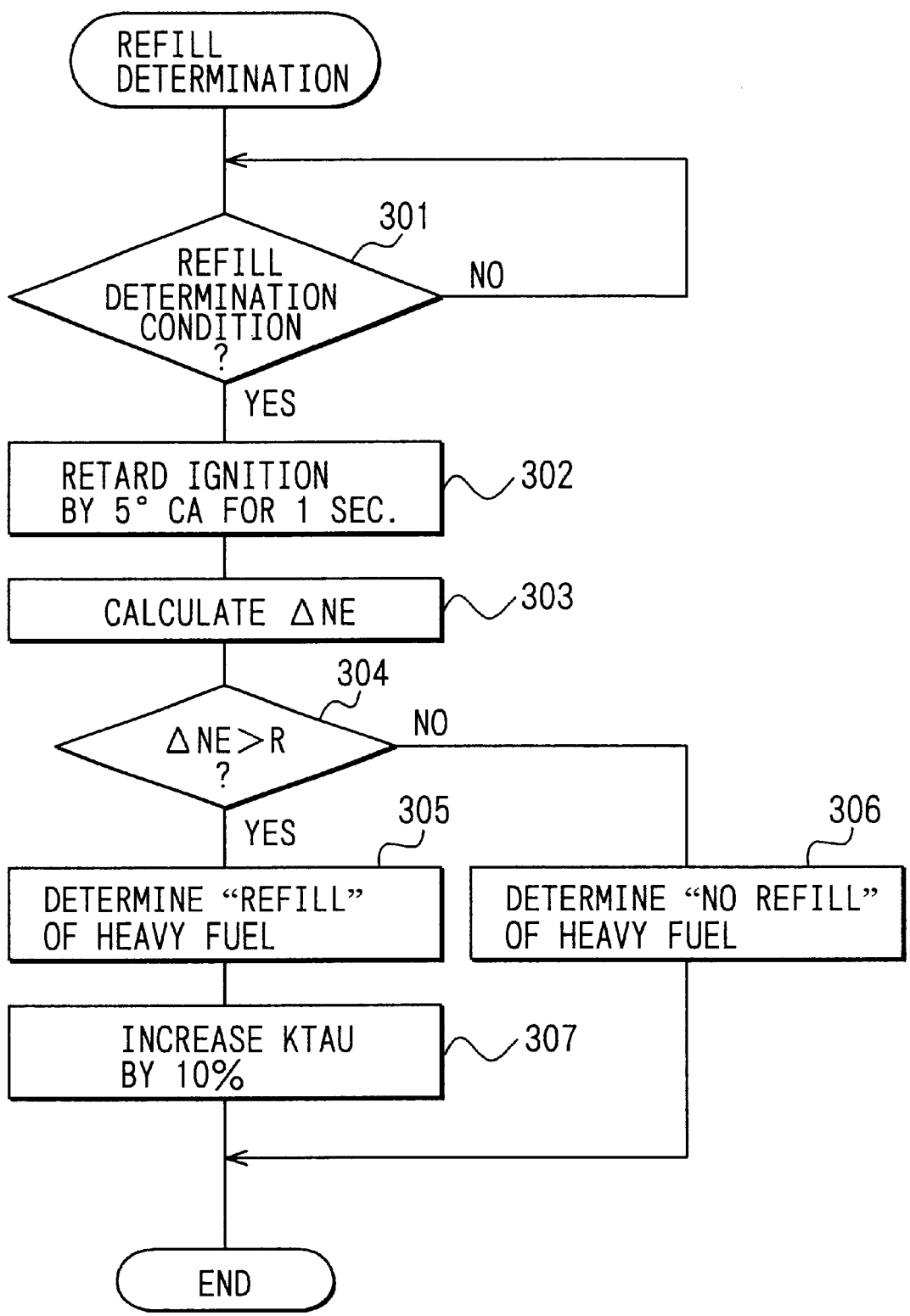
FIG. 6 is a flow diagram showing a refill determination processing executed in the first embodiment.

Then, the fuel correction processing shown in FIG. 5 is started at step 105. At this step 105, the fuel correction amount KTAU is calculated based on the fuel property value TNEN. The fuel refill processing shown in FIG. 6 is subsequently started at step 106.

It is checked at step 107 whether the air-fuel ratio sensor 30 has been activated or operative in the same manner as step 93 (FIG. 2). If the check result is NO (inoperative), the accumulated intake air amount TAF is calculated as follows at step 109 by adding the presently detected intake air amount AF to the previously calculated accumulated intake air amount TAF(i-1).

TAF(i)=TAF(i-1)+AF

Subsequently, the accumulated fuel injection amount TTAU from the engine starting is calculated as follows at step 110 by adding the presently calculated fuel injection amount TAU to the previously calculated accumulated injection amount TTAU(i-1).

TTAU(i)=TTAU(i-1)+TTAU

The above calculations at steps 109 and 110 are repeated so that the accumulated intake air amount TAF and the accumulated injection amount TTAU are updated every predetermined time or every angular rotation of the crankshaft.

If the check result at step 107 is YES (operative), the air-fuel ratio sensor 30 can detect the air-fuel ratio accurately. It is then checked at step 108 whether the detected air-fuel ratio has reached the target air-fuel ratio (14.7). As long as the check result at step 108 is NO, the steps 109 and 110 are repeated.

If the check result at step 108 changes to YES, the fuel property determination value TNEN is calculated as follows at step 111 (FIG. 4) from the accumulated intake air amount TAF and the accumulated injection amount TTAU.

TNEN=TTAU·14.7−TAF

In this equation, the product (TTAU 14.7) of the accumulated injection amount TTAU and the stoichiometric ratio (14.7) corresponds to the amount of air required to attain the complete combustion of air-fuel mixture in the cylinder. The difference TNEN between the product (TTAU 14.7) and the accumulated intake air amount TAF indicates the amount of fuel remaining on the inner wall of the intake port 12 as the fuel wet and did not contribute to the combustion in the cylinder. This value TNEN thus varies with the evaporative property of fuel, and indicates the fuel property quantatively.

The fuel property value TNEN may alternatively be calculated as follows.

TNEN=TTAU−TAF/14.7

In this equation, the division (TAF/14.7) corresponds to the amount of fuel which can be combusted completely with the accumulated intake air amount TAF. The difference TNEN between the accumulated fuel injection amount TTAU and the division (TAF/14.7) also indicates the amount of fuel remaining on the inner wall of the intake port 12 as the fuel wet and did not contribute to the combustion in the cylinder.

The fuel property value TNEN is corrected as follows at step 112 with the coolant temperature TW and the accumulated intake air amount TAF.

TNEN=TNEN·KTW·KTAF

Here, KTW indicates a correction coefficient variable with the coolant temperature TW, and may be mathematically calculated or determined based on the mapped data shown in FIG. 7A. Further, KTAF indicates a correction coefficient variable with the accumulated intake air amount TAF, and may be mathematically calculated or determined based on the mapped data shown in FIG. 7B.

The above correction of the fuel property value TNEN with KTW is for eliminating an influence of engine temperature on the fuel property value TNEN, because the vaporization of fuel also varies with the engine temperature. The above correction of the fuel property value TNEN with KTAF is for eliminating an influence of the pressure of intake air in the intake pipe 12, which is represented by the accumulated intake air amount TAF, because the vaporization of fuel also varies with the intake air pressure.

It is then checked at step 113 whether the fuel property value TNEN is larger than a comparison reference J. The comparison reference J may be fixed or varied with the coolant temperature TW as shown in FIG. 8. The comparison reference J is decreased as the coolant temperature TW increases, because the fuel becomes more evaporative as the coolant temperature TW increases. It is noted that the correction of TNEN with TW at step 112 may be eliminated as long as the comparison reference J is varied with the coolant temperature. Further, it is possible to vary the comparison reference J with the intake air pressure or accumulated intake air amount TAF, thereby eliminating the correction of TNEN with TAF at step 112.

If the check result at step 113 is YES (high TNEN), it is determined at step 114 that the fuel property is a "heavy" type. If the check result is NO (low TNEN), it is determined at step 115 that the fuel property is a "light" type. After the step 114 or 115, the flag is set to F=1 indicating that the fuel property has been determined, and stored in the back-up RAM 35 so that it may be referred to when the engine 11 is started next time.

The processing of fuel correction amount calculation executed at step 105 in FIG. 3 is shown in detail in FIG. 5.

In this processing of FIG. 5, it is first checked at step 201 whether the fuel property was determined to be heavy at the time of previous engine starting time. If the check result is NO (light fuel), the fuel correction amount KTAU corresponding to the fuel property is set to 0 (zero) so that the fuel injection amount TAU is not corrected with the correction amount KTAU because the fuel is sufficiently evaporative and does not remain long on the inner peripheral wall of the intake port or on the intake valve. If the check result at step 201 is YES (heavy fuel), the fuel injection amount TAU is corrected to increase in the following manner.

The fuel property value TNEN is read from the back-up RAM 35 at step 202, and is corrected as follows at step 203 based on the period lapsed after starting the engine 11.

TNEN=TNEN·KTIM

Here, KTIM indicates a correction factor varying with the post-start time period PST, and may be determined as shown in FIG. 9. The correction factor KTIM is set to be the largest immediately after the engine starting and to decrease as the time elapses so that the fuel injection amount is increased to attain the stoichiometric air-fuel ratio (14.7) at the earliest possible time while compensating the insufficient amount of fuel due to fuel wet in the intake port or on the intake valve. Further, because the fuel becomes more evaporative as the coolant temperature TW increases, that is, as the time elapses, the fuel correction amount (fuel enrichment) is gradually decreased. Thus, the air-fuel ratio is restricted from becoming too rich. The fuel correction amount KTAU is calculated based on the fuel property value TNEN. The fuel correction amount KTAU may be calculated mathematically or determined based on the mapped data.

At the following step 205, the accumulated fuel correction amount TKTAU is calculated as follows, by adding the presently calculated fuel correction amount KTAU to the previously calculated accumulated fuel correction amount TKTAU (i–1).

It is checked at step 206 whether the accumulated fuel correction amount TKTAU calculated from the engine start to the present time is compared with a comparison reference TK (TNEN) which is determined based on the fuel property TNEN. The comparison reference TK (TNEN) indicates the insufficient fuel amount, and may be calculated mathematically or by the use of mapped table data defined in relation to the fuel property value TNEN.

If the check result at step 206 is NO (insufficient fuel amount compensation), the above steps 203 to 205 are repeated to update the accumulated fuel correction amount TKTAU based on the fuel property value TNEN and the time after the engine starting. If the check result at step 206 is YES (sufficient amount compensation), the fuel correction amount KTAU is set to 0 (zero).

The processing of fuel refill determination executed at step 106 in FIG. 3 is shown in detail in FIG. 6.

In this processing of FIG. 6, it is first checked at step 301 whether fuel refill determination condition is satisfied. The determination condition may be an elapse of a predetermined time (for instance, 5 seconds) from the engine starting when the fuel property is determined to be heavy, and an elapse of a predetermined time (for instance, 5 seconds) from the start of fast catalyst heating operation.

If the check result at step 301 is YES, the ignition timing is retarded by 5° CA (crankshaft rotation angle) from the present ignition timing at step 302 for a predetermined period (for instance, 1 second). Then, a decrease in the engine rotation speed ΔNE for a predetermined period (for instance, 1 second) from the ignition timing retardation is calculated at step 303. The engine speed decrease ΔNE tends to increase as fuel property becomes heavy.

It is checked at step 304 whether the calculated engine speed decrease ΔNE is larger than a comparison reference R. This checking is for determining whether fuel which is heavier than the previous one is refilled. The comparison reference R may be a fixed value or variable with the coolant temperature TW or fuel temperature. The fuel becomes more evaporative as the coolant temperature TW increases, and hence the engine speed decrease ΔNE responsive to the ignition timing retardation is decreases. Therefore, the comparison reference R should be increased as the coolant temperature TW increases.

If the check result is NO (small decrease in engine speed), it is determined at step 306 that no refill of heavy fuel was made. If the check result at step 304 is YES (large decrease in engine speed), on the other hand, it is determined at step 305 that refill of heavier fuel was made. Then, at step 307, the fuel correction amount KTAU is increased by a predetermined rate (for instance, 10%).

Figure 10:
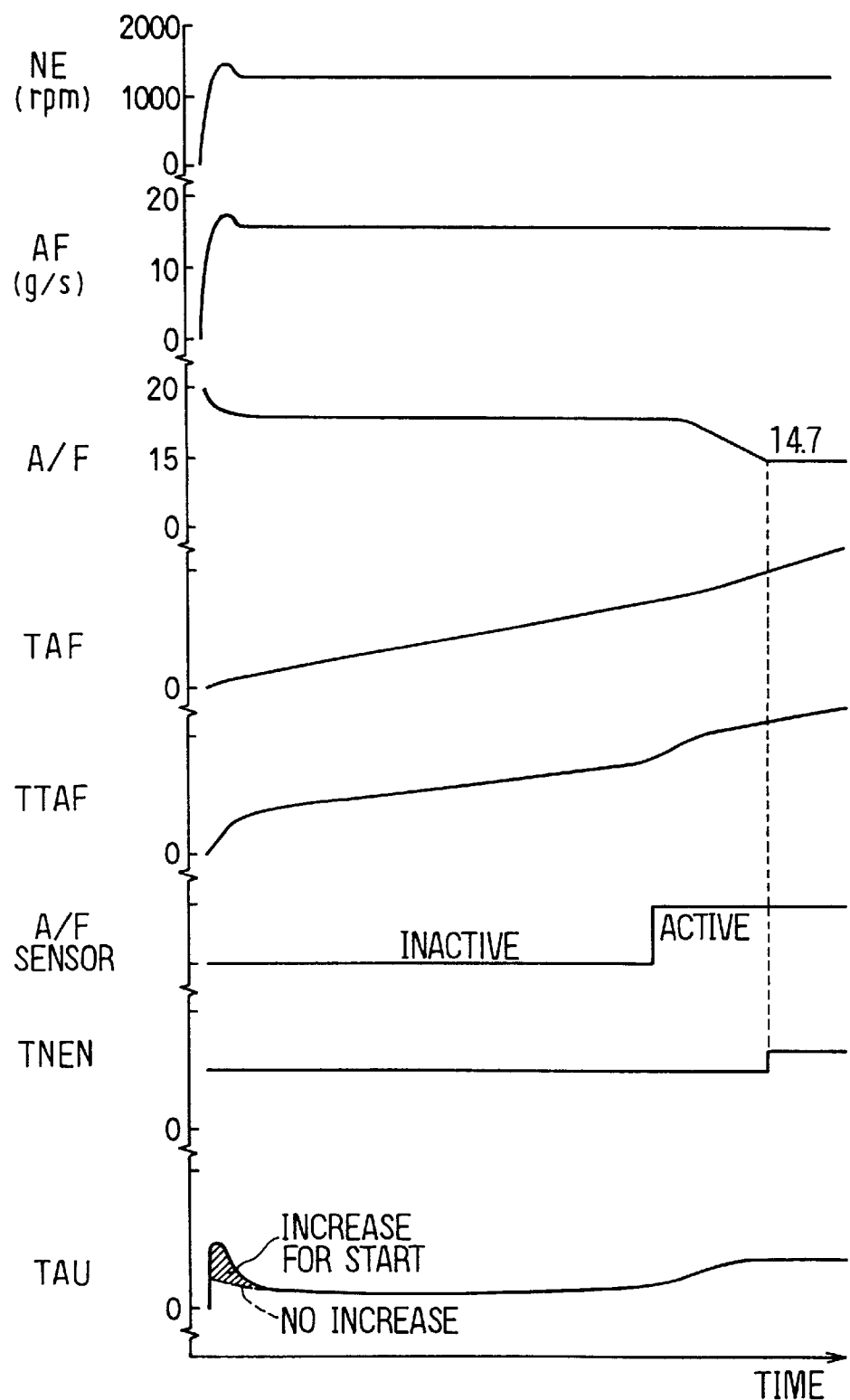
FIG. 10 is a timing diagram showing an operation of the first embodiment.

The operation of the first embodiment is shown in FIG. 10 with respect to the case in which the fuel was determined to be heavy at the time of previous engine starting. In the case of heavy fuel, the fuel injection amount at the time of engine starting is increased by the fuel correction amount KTAU in correspondence with the fuel property value TNEN. Thus, the insufficient amount of fuel can be added or compensated to attain the target air-fuel ratio (stoichiometric ratio) at the earliest time, and the combustion at the time of engine starting is stabilized quickly.

When the air-fuel ratio reaches the stoichiometric ratio (14.7) after the air-fuel ratio sensor 30 became activated, the fuel property value is calculated from the accumulated intake air amount TAF and the accumulated fuel injection amount TTAU. Then, the fuel property is determined form the calculated fuel property value TNEN.

As described above, the fuel property value TNEN is calculated form the accumulated intake air amount TAF and the accumulated fuel injection amount TTAU. Therefore, the fuel injection amount TAU can be increased to compensate for the fuel, which remains on the intake valve and the like and does not contribute the mixture combustion, immediately after the engine starting. Further, refill of heavy fuel is detected from the decrease in the engine speed by retarding the ignition timing after the engine starting. Therefore, the fuel injection amount can be increased from the engine starting immediately after refill of the heavy fuel, thus minimizing the influence of wet of heavy fuel. Further, as the target air-fuel ratio is set to the stoichiometric ratio before and after the air-fuel ratio sensor 30 is activated, it is possible to maintain the air-fuel ratio at around the stoichiometric ratio so that the catalyst in the catalytic converter 29 may operate with its highest purification efficiency.

Second Embodiment

Figure 11:
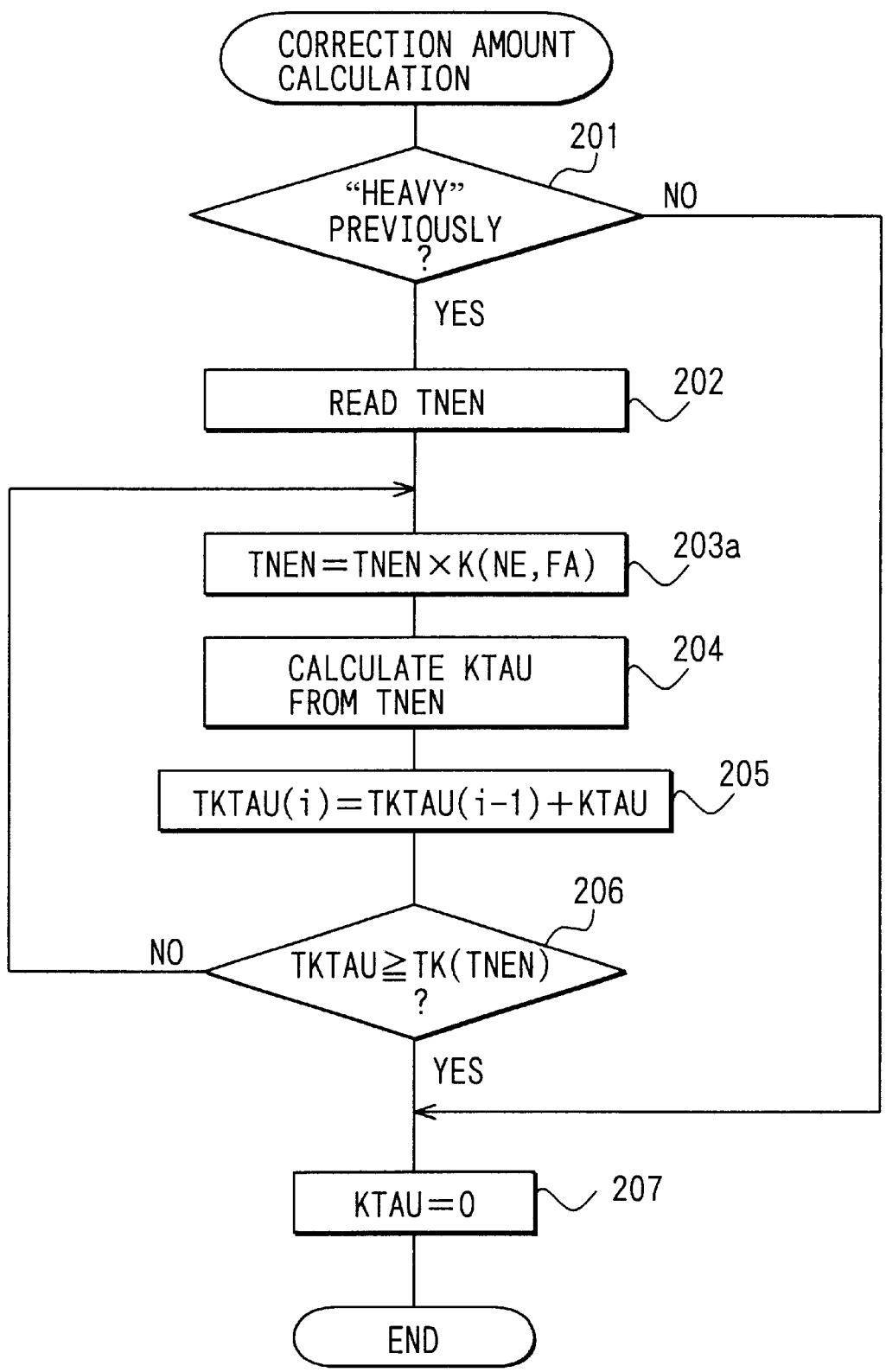
FIG. 11 is a flow diagram showing another correction amount calculation processing executed in a second embodiment of the present invention.

In a second embodiment, the processing of the fuel correction amount calculation shown in FIG. 5 is modified as shown in FIG. 11. Particularly, step 203 of FIG. 5 is modified to step 203a.

At step 203a, the fuel property value TNEN is calculated based on the engine rotation speed NE and the intake air amount AF as follows. Here, K(NE, AF) is a correction coefficient which varies with NE and FA, and may be calculated mathematically or by the use of mapped data shown in FIG. 12.

TNEN=TNEN·K(NE, AF)

This modification is based on the finding that the vaporization of fuel changes with the pressure of intake air in the intake pipe 12, and the intake pressure is represented as a function of the engine rotation speed NE and the intake air amount AF. Thus, the fuel correction amount KTAU is corrected based on the intake air pressure. Therefore, the fuel correction amount KTAU can be calculated in correspondence with post-start engine operating conditions even when the engine operating conditions change.

In the second embodiment, it is possible to detect the intake air pressure by a pressure sensor and correct the fuel property value TNEN with the detected intake air pressure. Further, the fuel correction amount KTAU may be directly corrected, in place of correcting the fuel property value, based on the intake air pressure and the post-start elapsed time.

Third Embodiment

Figure 13:
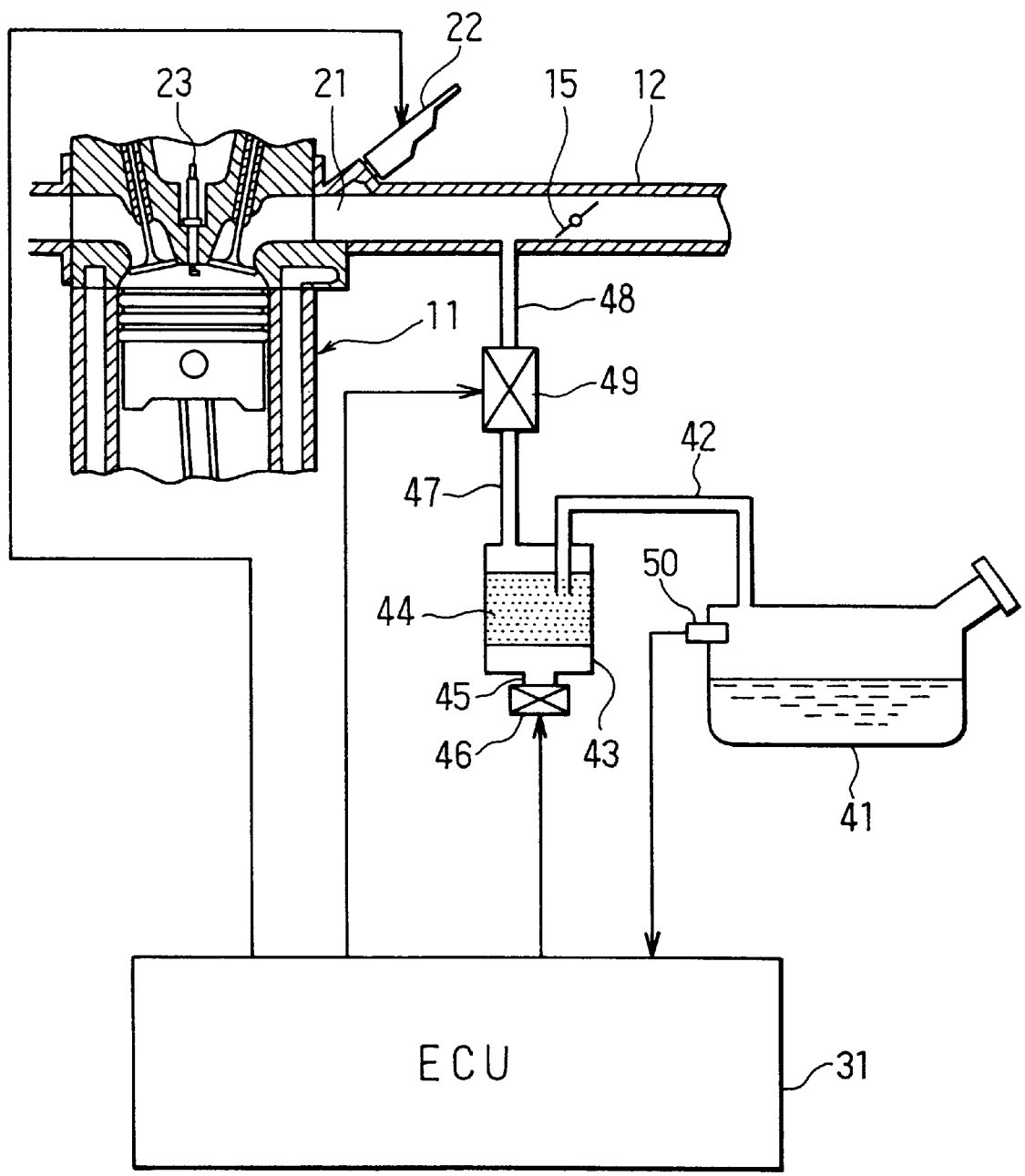
FIG. 13 is a schematic view showing another engine control system which employs a fuel property determination method and apparatus according to a third embodiment of the present invention.

In a third embodiment shown in FIG. 13, the fuel property is determined based on an increase in a pressure inside a fuel tank.

As shown in FIG. 13, a fuel tank 41 is connected to a canister 43 via a connection pipe 42. The canister 43 accommodates therein an adsorbent 44 such as activated carbon or the like which adsorbs evaporated fuel gas. The canister 43 has an air vent pipe 45 which is opened or closed to atmosphere by a vent valve 46 driven by the ECU 31. Purge pipes 47 and 48 are provided between the canister 43 and the intake pipe 12 to purge the adsorbed evaporated fuel gas from the canister 43 into the intake pipe 12. A purge control valve 49 driven by the ECU 31 is provided to control the amount of purging the evaporated fuel gas. A pressure sensor 50 is provided to detect the pressure P in the fuel tank 41.

Figure 14:
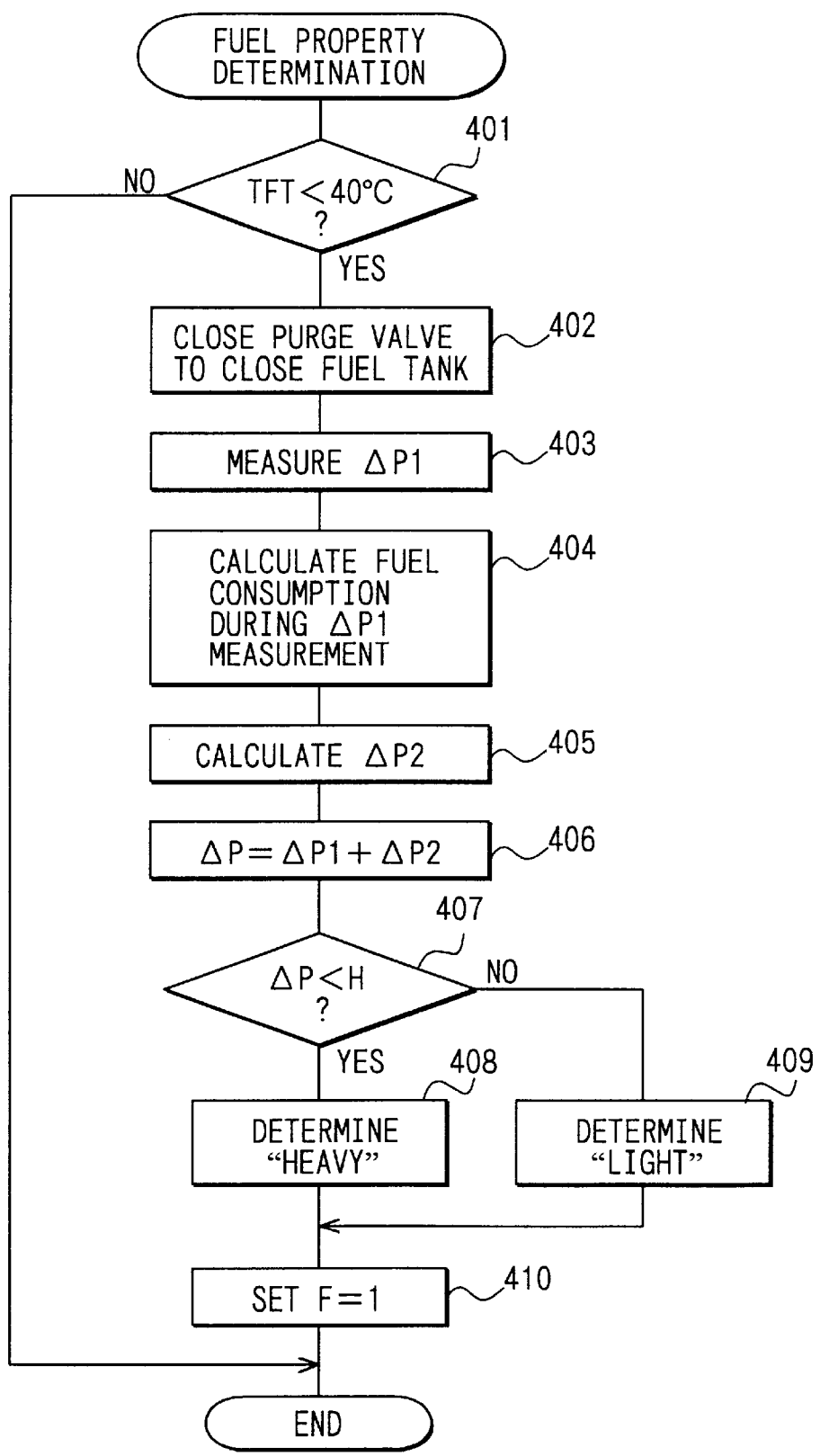
FIG. 14 is a flow diagram showing a further fuel property determination processing executed in the third embodiment.

In the third embodiment, the fuel property is determined by the ECU 31 as shown in FIG. 14. This fuel property determination processing is initiated every engine starting or every predetermined timing (before completion of engine warm-up) after the engine starting.

It is first checked at step 401 whether a temperature TFT inside the fuel tank 41 is lower than a comparison reference (for instance, 40° C.). The temperature TFT may be detected by a temperature sensor (not shown) provided in the fuel tank 41 or may be estimated from the coolant temperature TW detected at the time of engine starting and the post-start elapsed time. For instance, the fuel temperature TFT may be estimated as being lower than 40° C., if the coolant temperature TW at the engine starting is below 35° C. and the post-start elapsed time is less than a predetermined period.

If the check result at step 401 is NO (low fuel temperature), this processing ends immediately. This is because the fuel becomes more evaporative as the fuel temperature rises, and a difference between the amounts of fuel evaporation (difference between the pressure increases in the tank) is reduced. The fuel refill will not be detected accurately if the fuel temperature is high.

If the check result at step 401 is YES (low fuel temperature), both the vent valve 46 and the purge control valve 49 are closed at step 402 to fully close the fuel tank 41. Then a pressure increase $\Delta P1$ in the tank 41 within a predetermined period is measured at step 403.

The amount of fuel consumed during the period of measuring the pressure increase $\Delta P1$ is calculated at step 404, and a pressure decrease $\Delta P2$ in the tank 41 caused by the consumed fuel CF is calculated at step 405. A pressure increase $\Delta P$ in the tank 41, which is actually caused by the evaporation of fuel, is calculated as follows at step 406 by correcting the calculated pressure increase $\Delta P1$ with the pressure decrease $\Delta P2$.

$$\Delta P = \Delta P1 + \Delta P2$$

The pressure increase $\Delta P$ which is actually caused by the evaporation of fuel may alternatively calculated as follows from the pressure increase $\Delta P1$, tank space volume TSV which is not filled with fuel, and the consumed fuel CF. Here, the tank space volume TSV may be calculated from the amount of fuel remaining in the tank 41.

$$\Delta P = \Delta P1 \cdot (TSV + CF)/TSV$$

Then, it is checked at step 407 whether the calculated pressure increase $\Delta P$ is less than a comparison reference H. This comparison reference may be a fixed value or may be calculated mathematically or by the use of mapped data to vary with the coolant temperature TW or fuel temperature. The comparison reference H should be increased as the coolant temperature TW rises, because the fuel becomes more evaporative to increase the pressure increase $\Delta P$ as the coolant temperature TW rises.

If the check result at step 407 is YES (small pressure increase), it is determined at step 408 that the fuel-property is a "heavy" type. If the check result at step 407 is NO (large pressure increase), it is determined at step 409 that the fuel property is a "light" type.

Then, the fuel property determination flag is set to F=1 at step 410 and stored to indicate that the fuel property has been determined. It is to be noted that the determination result of fuel property, for instance, the pressure increase $\Delta P$ may be used to correct the fuel injection amount as in the foregoing embodiments.

According to the third embodiment, the fuel property can be determined accurately, because the pressure increase $\Delta P$ is calculated by correcting the pressure increase $\Delta P1$ with the pressure decrease $\Delta \Delta P2$ which corresponds to the consumed fuel amount. It is of course possible to determine the fuel property from the pressure increase $\Delta P1$ without using the pressure decrease $\Delta P2$.

The present invention should not be limited to the above disclosed embodiments, but may be implemented in many other ways without departing from the spirit of the invention.

What is claimed is:

1. An apparatus for determining property of fuel supplied to an engine comprising:

an air-fuel ratio-sensor for detecting an air-fuel ratio of air-fuel mixture supplied to an engine;

accumulated intake air amount calculation means for calculating an accumulated amount of air supplied to the engine for a predetermined period from a time of starting the engine to a time of an output of the air-fuel ratio sensor indicative of reaching a target air-fuel ratio;

accumulated fuel amount calculation means for calculating an accumulated amount of fuel supplied to the engine for the predetermined period; and fuel property determination means for determining fuel property based on a fuel property value which is a predetermined function of the calculated accumulated intake air amount and the calculated accumulated fuel amount.

2. The apparatus as in claim 1, wherein:

the time of the output of the air-fuel ratio sensor is after an activation of the air-fuel ratio sensor; and the fuel property determination means calculates the fuel property value from a difference between the calculated accumulated intake air amount and a product of the calculated accumulated fuel amount and the target air-fuel ratio, and determines the fuel property from the calculated fuel property value.

3. The apparatus as in claim 1, wherein:

the fuel property determination means corrects the calculated fuel property value with a parameter variable with a coolant temperature of the engine.

4. The apparatus as in claim 1, further comprising:

fast catalyst heating means for retarding an ignition timing for starting the engine under a cold temperature condition thereby to heat an exhaust purifying catalyst quickly, wherein the fast catalyst heating means includes means for reducing an amount of retardation of the ignition timing for starting the engine under the cold temperature condition next time, when the fuel property determination means determines that the fuel is a heavy type.

5. The apparatus as in claim 1, further comprising:

fuel correction means for correcting, based on a fuel property determination that the fuel is a heavy type, the amount of fuel to be supplied to the engine in a next starting of the engine.

6. The apparatus as in claim 5, wherein:

the fuel correction means gradually decreases an amount of correcting the amount of fuel as an elapse of time after starting the engine.

7. The apparatus as in claim 5, wherein:

the fuel correction means corrects an amount of correcting the amount of fuel based on a rotation speed and an intake condition of the engine.

8. The apparatus as in claim 5, wherein:

the fuel correction means stops correcting the amount of fuel, when an accumulated amount of correcting the fuel amount from starting the engine reaches a predetermined value determined based on the calculated fuel property value.

9. The apparatus as in claim 1, further comprising:

refill determination means for retarding an ignition timing of the engine after starting the engine, and determining a refill of fuel of different property based on a decrease in a rotation speed of the engine resulting from a retardation of the ignition timing.

10. The apparatus as in claim 9, further comprising:

fuel increasing means for increasing the amount of fuel to be supplied to the engine in response to a determination of refill of a heavy type fuel.

11. The apparatus as in claim 1, further comprising:

open-loop control means for calculating the amount of fuel irrespective of the output of the air-fuel ratio sensor until the air-fuel ratio senor is activated, so that the air-fuel ratio of the air-fuel mixture supplied to the engine is controlled around the target air-fuel ratio; and closed-loop control means for calculating the amount of fuel supplied to the engine in response to the output of the air-fuel ratio sensor after the air-fuel ratio sensor is activated, so that the air-fuel ratio of the air-fuel ratio mixture supplied to the engine is feedback-controlled to the target air-fuel ratio.

12. A method of controlling an engine having a cylinder comprising:

starting an engine;

measuring an amount of intake air supplied to the engine;

injecting fuel to the engine in an amount calculated in correspondence with the measured intake air amount;

estimating an amount of fuel injected to the engine but remaining upstream the cylinder;

determining fuel property based on the estimated amount of fuel remaining upstream the cylinder;

storing the determined fuel property after the engine is stopped; and correcting the amount of injected fuel based on the stored fuel property when the engine is started again after stopped once.

13. The method as in claim 12, wherein the estimating includes:

accumulating the measured amount of intake air and the amount of injected fuel, respectively, for a predetermined period from a time of starting the engine to a time of an output of an air-fuel ratio sensor indicative of reaching a target air-fuel ratio; and determining a relationship between the accumulated amount of intake air and the accumulated amount of injected fuel, so that the amount of fuel remaining upstream the cylinder is estimated from the determined relationship.

14. The method as in claim 13, wherein:

the relationship is determined as a difference between the accumulated amount of measured intake air and a product of the accumulated amount of injected fuel and the target air-fuel ratio.

15. The method as in claim 14, wherein:

the difference is corrected with a parameter variable with a coolant temperature of the engine.

16. The method as in claim 12, wherein:

the amount of fuel to be injected to the engine in a next starting of the engine is increased when the stored fuel property is indicative of a heavy-type of fuel.

17. The method as in claim 16, wherein:

an amount of increase in the fuel injected in the next starting of the engine is gradually decreased as an elapse of time after starting the engine.

18. The method as in claim 12, further comprising:

retarding an ignition timing of the engine after starting the engine;

determining a refill of fuel of different property based on a decrease in a rotation speed of the engine resulting from a retardation of the ignition timing; and increasing the amount of injected fuel in response to a determination of refill of a heavy type fuel.

* * * * *